US009248249B2

(12) United States Patent
Li et al.

(10) Patent No.: US 9,248,249 B2
(45) Date of Patent: Feb. 2, 2016

(54) POINT-OF-CARE PATHOGEN MONITORING DEVICES AND SYSTEMS

(75) Inventors: Youzhi Li, Longmont, CO (US); Bo Chen, Louisville, CO (US)

(73) Assignee: Covidien LP, Mansfield, MA (US)

( * ) Notice: Subject to any disclaimer, the term of this patent is extended or adjusted under 35 U.S.C. 154(b) by 1409 days.

(21) Appl. No.: 12/480,377

(22) Filed: Jun. 8, 2009

(65) Prior Publication Data
US 2010/0307507 A1   Dec. 9, 2010

(51) Int. Cl.
*A61M 16/04* (2006.01)
*A61B 10/00* (2006.01)

(52) U.S. Cl.
CPC ....... *A61M 16/0463* (2013.01); *A61M 16/0479* (2014.02); *A61M 16/0484* (2014.02); *A61B 10/0051* (2013.01); *A61B 2010/0061* (2013.01); *A61M 16/0434* (2013.01)

(58) Field of Classification Search
CPC ............ A61M 16/04; A61M 16/0402; A61M 16/0404; A61M 16/0409; A61M 16/0415; A61M 16/0463; A61M 16/0475; A61M 16/0477; A61M 16/0486; A61M 16/0481; A61M 16/0484; A61B 2010/0225; A61B 10/0096
USPC ................................ 600/573, 581, 584; 435/5
See application file for complete search history.

(56) References Cited

U.S. PATENT DOCUMENTS

| | | | | |
|---|---|---|---|---|
| 5,501,215 A | * | 3/1996 | Huerta ...................... | 128/207.15 |
| 5,775,325 A | * | 7/1998 | Russo ....................... | 128/205.12 |
| 5,819,723 A | * | 10/1998 | Joseph ...................... | 128/207.14 |
| 5,927,273 A | * | 7/1999 | Federowicz et al. ...... | 128/200.24 |
| 6,092,530 A | | 7/2000 | Weissman et al. | |
| 6,315,739 B1 | | 11/2001 | Merilainen et al. | |
| 6,460,540 B1 | * | 10/2002 | Klepper .................... | 128/207.14 |
| 7,273,050 B2 | | 9/2007 | Wei | |
| 7,654,264 B2 | * | 2/2010 | Clayton .................... | 128/207.15 |
| 2004/0011358 A1 | * | 1/2004 | Smaldone et al. ........ | 128/200.24 |
| 2005/0279360 A1 | | 12/2005 | Wei | |
| 2006/0107962 A1 | * | 5/2006 | Ward et al. ................ | 128/207.14 |
| 2007/0089748 A1 | * | 4/2007 | Madsen et al. ............ | 128/207.15 |
| 2007/0213632 A1 | * | 9/2007 | Okazaki et al. ............... | 600/562 |
| 2007/0299357 A1 | * | 12/2007 | Villegas ......................... | 600/529 |
| 2008/0011304 A1 | | 1/2008 | Stewart | |
| 2008/0019866 A1 | * | 1/2008 | Paek et al. ......................... | 422/55 |
| 2008/0241858 A1 | * | 10/2008 | Metzger et al. ................. | 435/7.2 |
| 2009/0038620 A1 | * | 2/2009 | Efrati ......................... | 128/207.14 |

(Continued)

OTHER PUBLICATIONS

Bassi, Gianluigi Li et al.; "Following tracheal intubation, mucus flow is reversed in the semirecumbent position: Possible role in the pathogenesis of ventilator-associated pneumonia"; Crit Care Med 2007, vol. 36, No. 2, pp. 518-525.

(Continued)

*Primary Examiner* — Adam J Eiseman
(74) *Attorney, Agent, or Firm* — Fletcher Yoder PC

(57) ABSTRACT

Various embodiments of a secretion collection and/or sample analysis device are provided for point-of-care collection and/or analysis of secretions collected from the airways of intubated patients. The disclosed embodiments include a variety of placements of the device with respect to a tracheal tube that include in a secretion reservoir, between an evacuation conduit and the secretion reservoir, and connected in series after the evacuation conduit and the secretion reservoir. Certain embodiments may include a lab-on-a-chip device that analyzes secretions via polymerase chain reaction (PCR) based DNA sequencing.

9 Claims, 5 Drawing Sheets

(56) References Cited

U.S. PATENT DOCUMENTS

| | | | |
|---|---|---|---|
| 2010/0170517 A1* | 7/2010 | Hackner | 128/207.14 |
| 2010/0200428 A1* | 8/2010 | Choi et al. | 205/777.5 |
| 2012/0090620 A1* | 4/2012 | Deutsch | 128/207.15 |

OTHER PUBLICATIONS

Lazcka, Olivier et al.; "Pathogen detection: A perspective of traditional methods and biosensors"; ScienceDirect; Biosensor & Bioelectronics 22 (2007) 1205-1217.

Lee, Jeong-Gun et al.; "Microchip-based one step DNA extraction and real-time PCT in one chamber for rapid pathogen identification"; Lab Chip, 2006, 6, 886-895.

Liao, Joseph C. et al.; "A Point-of-Care Micro-Laboratory for Direct Pathogen Identification in Body Fluids"; IEEE Nanotechology Council Review on Advance of Micro, Nano, and Molecular Genomics Research, 2006, 6, 5 pgs.

Lin, Baochuan et al.; "Broad-spectrum respiratory tract pathogen identification using resequencing DNA microarrays"; Genomics Research, 2006 16: 527-535.

Mariella, Jr., Raymond; "Sample preparation: the weak link in microfluidics-based biodetection"; Biomed Microdevices (2008) 10:777-784.

Ohno, Ken-Ichi et al.; "Microfluidics: Applications for analytical purposes in chemistry and biochemistry"; Electrophoresis 2008, 29, 4443-4453.

Schulze, Holger et al.; "Multiplexed optical pathogen detection with lab-on-a-chip devices"; J. Biophoton, 2, No. 4, 199-211 (2009).

Zaytseva, Natalya V.; "Development of a microfluidic biosensor module for pathogen detection"; Lab Chip, 2005, 5, 805-811.

Grap, Mary Jo E.; "A Peri-Intubation Oral intervention to Reduce Oral Flora and VAP"; (NCT00248300); Virginia Commonwealth University, Nov. 2, 2005; 4 pgs.

Mohamed, Afaf; "Effect of Gravity on Tracheal Colonization During Mechanical Ventilation in Infants"; (NCT00491660); Cairo University Children's Hospital, Cairo, Egypt, Jun. 5, 2007, 3 pgs.

Stone, Robert H.; "Removal of Endotracheal Tube Secretions Comprehensively Until Extubation (RESCUE)", (NCT00663637); O.M. Neotech, Inc., Apr. 18, 2008; 3 pgs.

Sanchez, Miguel; "Prevention of Pneumonia Comparing Ceftriazone With Subglottic Aspiration"; Hospital Principe de Asturias, Spain, Sep. 11, 2006, 4 pgs.

* cited by examiner

POINT-OF-CARE PATHOGEN MONITORING DEVICES AND SYSTEMS

BACKGROUND

The present disclosure relates generally to medical devices and, more particularly, to airway devices, such as tracheal tubes.

This section is intended to introduce the reader to aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Tracheal tubes are often placed in the airway of a patient in medical situations that necessitate protection of the airway from possible obstruction or occlusion. For instance, tracheal tubes may be used in emergency situations, such as when a patient experiences cardiac or respiratory arrest. Such intubations increase a patient's risk of developing ventilator-associated pneumonia (VAP) due to bacterial colonization of the lower respiratory airways. In healthy individuals, mucociliary clearance removes particles and microorganisms prior to respiratory infection. However, in critically ill patients, clearance mechanisms are compromised due to tracheal tube cuff inflation, and mucus accumulates around the cuff. In many instances, such critically ill patients may remain intubated for extensive periods of time, during which mucus accumulated at the bottom of the cuff may drop to the proximal trachea and ultimately infect the lungs.

Traditionally, VAP development in the lungs may be one of the primary causes of morbidity and mortality in critically ill patients. Accordingly, early detection of the presence of pathogens responsible for VAP may decrease morbidity and mortality in some patients. A traditional diagnosis of VAP may rely on the collection of sputum samples using invasive devices and techniques, such as a bronchoscope. Collected samples must then be sent to an offsite laboratory for culturing and analysis. Typical analysis may require a few days for results to be generated, thus leaving the patient susceptible to VAP development and other complications. For instance, pathogens may be detected in a sample that is a few days old, thus delaying necessary treatment and allowing pathogens to further multiply and develop in the patient. Accordingly, it is now recognized that there exists a need for quicker detection and analysis of pathogens responsible for VAP.

BRIEF DESCRIPTION OF THE DRAWINGS

Advantages of the present disclosure may become apparent upon reading the following detailed description and upon reference to the drawings in which.

DETAILED DESCRIPTION OF SPECIFIC EMBODIMENTS

Figure 1:
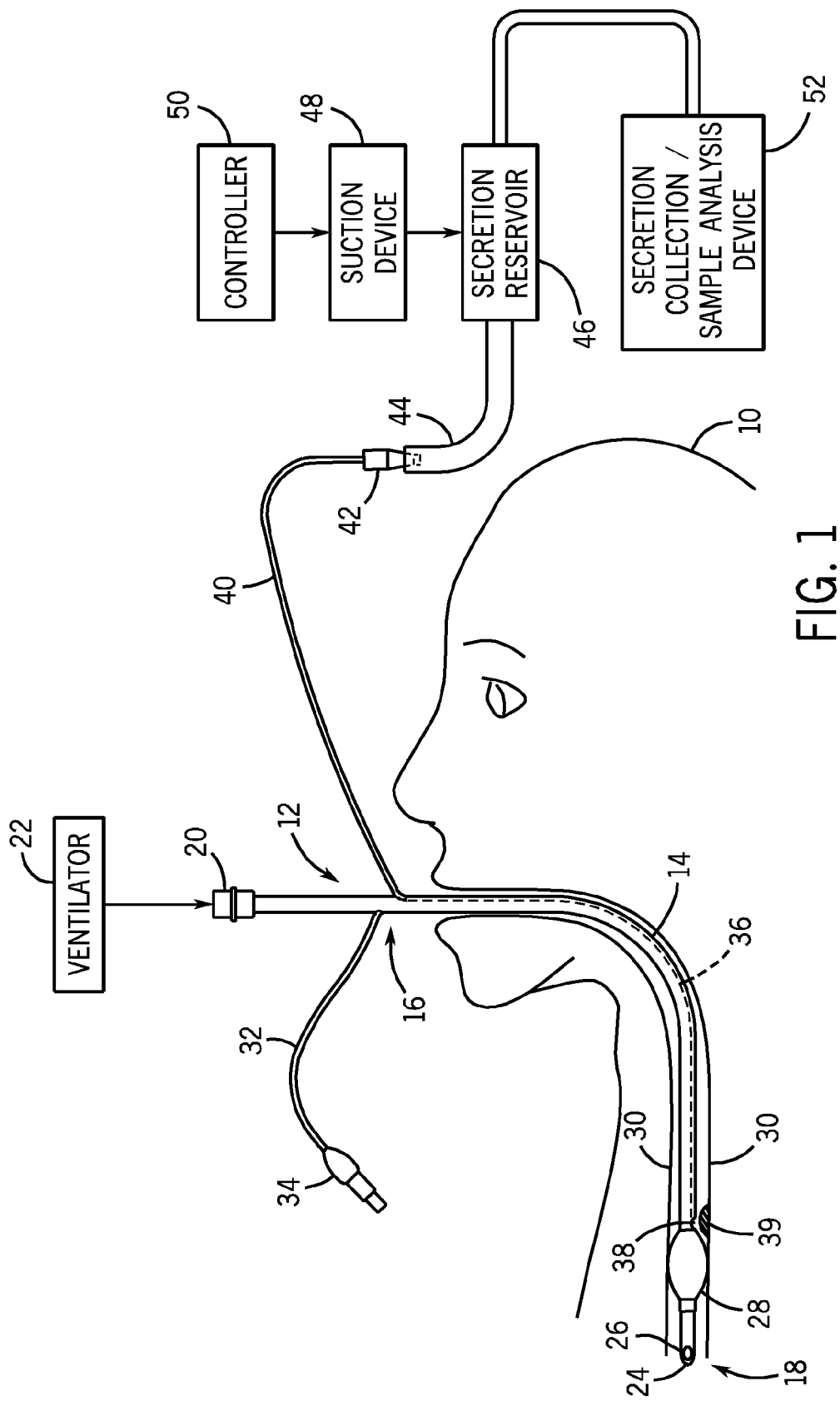
FIG. 1 illustrates an exemplary system including an endotracheal tube connected to a secretion collection and/or sample analysis device through a secretion reservoir in accordance with aspects of the present disclosure.

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As discussed in further detail below, various embodiments of a secretion collection and/or sample analysis device (hereinafter "device") are provided for point-of-care collection and/or analysis of secretions collected from the airways of intubated patients. The device is capable of collecting and/or analyzing secretion samples at the point-of-care rather than in an offsite laboratory, capable of being connected to an endotracheal tube via an evacuation conduit, able to be inserted into a secretion reservoir, and so forth. The disclosed embodiments include a variety of placements of the device with respect to a tracheal tube that include in the secretion reservoir, between the evacuation conduit and the secretion reservoir, and connected in series after the evacuation conduit and the secretion reservoir. Certain embodiments may include a lab-on-a-chip device that analyzes secretions via polymerase chain reaction (PCR) based DNA sequencing. The foregoing features, among others, may have the effect of shortening the time between sample collection and analysis, thereby allowing treatment of patients testing positive for VAP pathogens sooner than is traditionally possible.

The devices and techniques provided herein may be used as a stand alone system or in conjunction with an analysis system. For instance, certain embodiments may provide a unit that receives and processes multiple devices at a central location in the care giving facility. Control panels integral to the unit may provide the user the flexibility to enter patient information, choose which program to execute, start/stop the analysis, and so forth. In certain embodiments, the provided devices may be used in conjunction with auxiliary devices, such as vacuums, ventilators, humidifiers, and so forth. A controller may be connected to such auxiliary devices to control the timing of the secretion collection, correlate secretion collection with patient expiration, and so forth. The controller may include memory, which may be volatile or non-volatile memory, such as read only memory (ROM), random access memory (RAM), magnetic storage memory, optical storage memory, or a combination thereof. Furthermore, a variety of control parameters may be stored in the memory along with code configured to provide a specific output (e.g., apply vacuum every 10 seconds, purge the system after each sample is collected, and so forth) during operation.

Turning now to the drawings, FIG. 1 illustrates an exemplary system including a patient 10 intubated with an endotracheal tube 12 in accordance with aspects of the present disclosure. The endotracheal tube 12 includes a central tubular body 14 with proximal and distal ends 16 and 18, respectively. In the illustrated embodiment, the proximal end 16 is outfitted with a connector 20 that may be attached to a mechanical ventilator 22 during operation. The distal end 18 terminates in an opening 24 and may be placed in a patient's trachea during operation to maintain airflow to and from the patient's lungs. A Murphy's eye 26 may be located on the tubular body 14 opposite the opening 24 to prevent airway occlusion when the endotracheal tube 12 is improperly placed within the trachea of the patient.

As illustrated, a cuff 28 that may be inflated to seal against the walls 30 of a body cavity (e.g., a trachea) may be attached to the distal end 18 of the tubular body 14. The cuff 28 may be inflated via an inflation lumen 32 terminating in a fixture 34 located at the proximal end 16 of the tubular body 14. The tubular body 14 may also include a suction lumen 36 that extends from a location on the endotracheal tube 12 positioned outside the body when in use to a location around the cuff 28 inside the body. The suction lumen 36 may terminate in a port 38 through which accumulated secretions 39 may be aspirated. In the illustrated embodiment, the single port 38 is located directly above the cuff 28. However, in other embodiments, one or more ports may be located anywhere along the length of the tubular body 14 such that they aspirate secretions from the airway of the patient 10. An exterior suction tube 40 connects to the suction lumen 36 for the removal of suctioned fluids. The suction tube 40 terminates outside the body in a fixture 42 that allows the suction tube 40 to be connected to auxiliary equipment (e.g., vacuum, collection reservoir, and so forth) during suctioning.

In the illustrated embodiment, the suction tube 40 is connected to an evacuation conduit 44 through which secretions may flow during operation. As illustrated, the evacuation conduit 44 empties into a secretion reservoir 46 that is configured to collect secretions and may be emptied or replaced as desired. During operation, a suction device 48 may be connected to the secretion reservoir 46 to apply suction to the evacuation conduit 44 and aspirate secretions from the airway of the patient. A controller 50 may be connected to the suction device 48 to control the timing of the secretion collection, correlate secretion collection with patient expiration, and so forth. For instance, vacuum may be applied such that mucus flow through the suctioning lumen 36 is established in the same direction and at the same time as airflow out of the patient during expiration. The controller 50 may include memory, which may be volatile or non-volatile memory, such as ROM, RAM, magnetic storage memory, optical storage memory, or a combination thereof. Furthermore, a variety of control parameters may be stored in the memory along with code configured to provide a specific output (e.g., apply vacuum every 10 seconds, purge the system after each sample is collected, and so forth) during operation.

A secretion collection and/or sample analysis device 52 may receive secretion samples from the secretion reservoir 46 during operation. In some embodiments, the device 52 may be configured to collect secretion samples at predetermined time points over a preset period of time. For instance, the device 52 may be configured to collect a sample from the secretion reservoir 46 every ten seconds for ten minutes. In certain embodiments, the device 52 may be configured to both collect and analyze the secretion samples at the point-of-care. For instance, the device 52 may be a "lab-on-a-chip," which may include a microfluidic genetic analysis system capable of performing PCR-based DNA sequencing. The device 52 may be configured in accordance with generally known technologies, such as those taught by the following: Lin, B., Wang, Z., Vora, G. J., et al. 2006. Broad-spectrum respiratory tract pathogen identification using resequencing DNA microarrays. *Genome Res.* 16: 527-535; Liao, J. C., Ma, Y., Gau, V., et al. 2006. A point-of-care micro-laboratory for direct pathogen identification in body fluids. *Nano/Micro Eng. and Mol. Sys.* 1109-1112; Zaytseva, N. V., Goral, V. N., Montagna, R. A., et al. 2005. Development of a microfluidic biosensor module for pathogen detection. *Lab Chip* 5: 805-811; Lee, J., Cheong, K. W., Huh, N., et al. 2006, Microchip-based one step DNA extraction and real-time PCR in one chamber for rapid pathogen identification. *Lab Chip* 6: 886-895. All of these are hereby incorporated herein by reference. Pathogen specific probes may be desired for specific bacteria, particularly VAP pathogens, which may be developed in accordance with known procedures. Accordingly, in some embodiments, the lab-on-a-chip may contain probes for DNA sequences unique to the pathogens responsible for VAP. Such a device 52 offers distinct advantages over traditional systems since both collection and analysis of the secretion samples may be performed at the care giving facility in a single day. The traditional time gap, which may span up to a week, between sample collection at the bedside and sample analysis at an offsite lab may be eliminated, which may reduce the amount of time patients testing positive for the presence of pathogens must wait for treatment.

Figure 2:
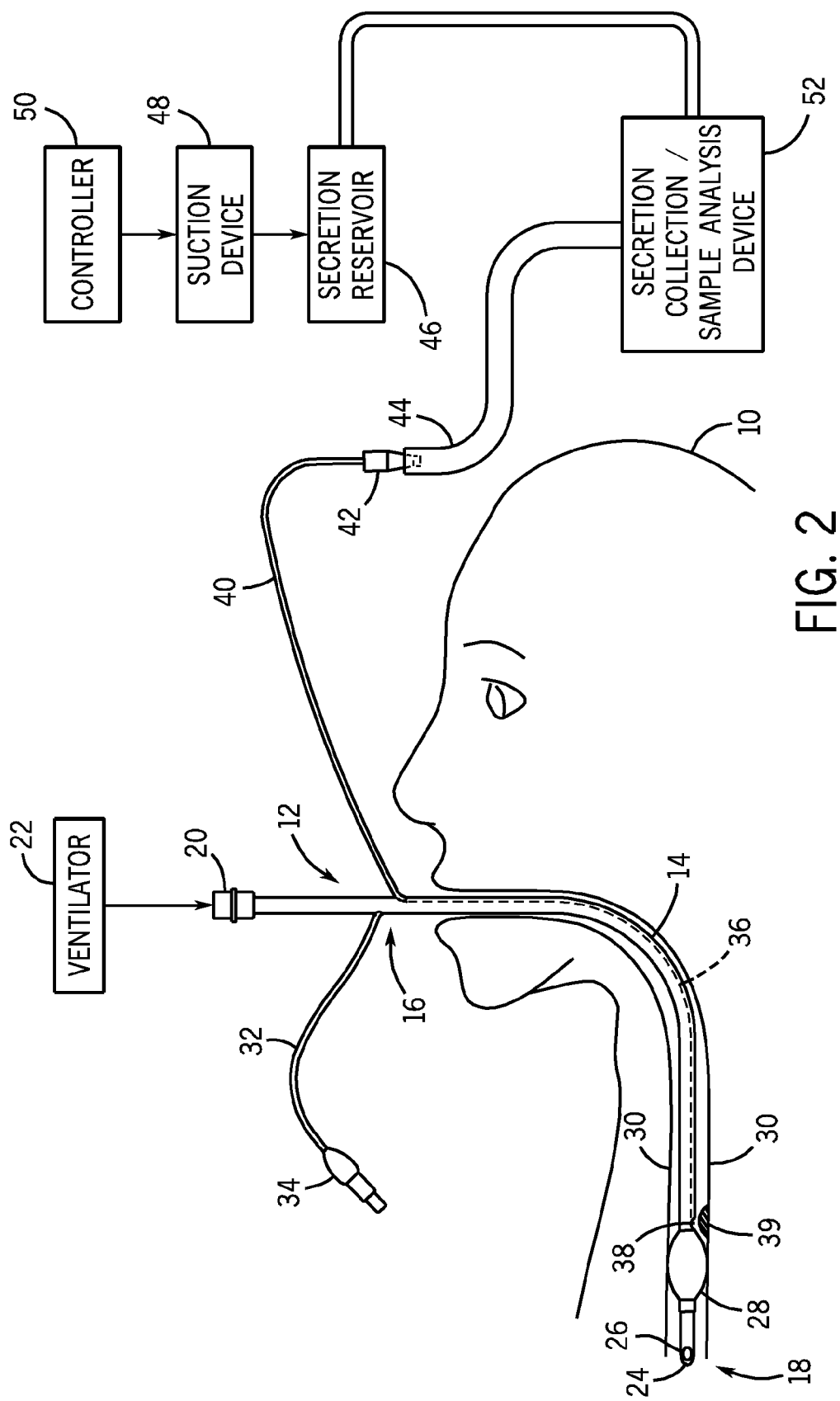
FIG. 2 illustrates an exemplary system including an endotracheal tube directly connected to a secretion collection and/or sample analysis device in accordance with aspects of the present disclosure.
Figure 3:
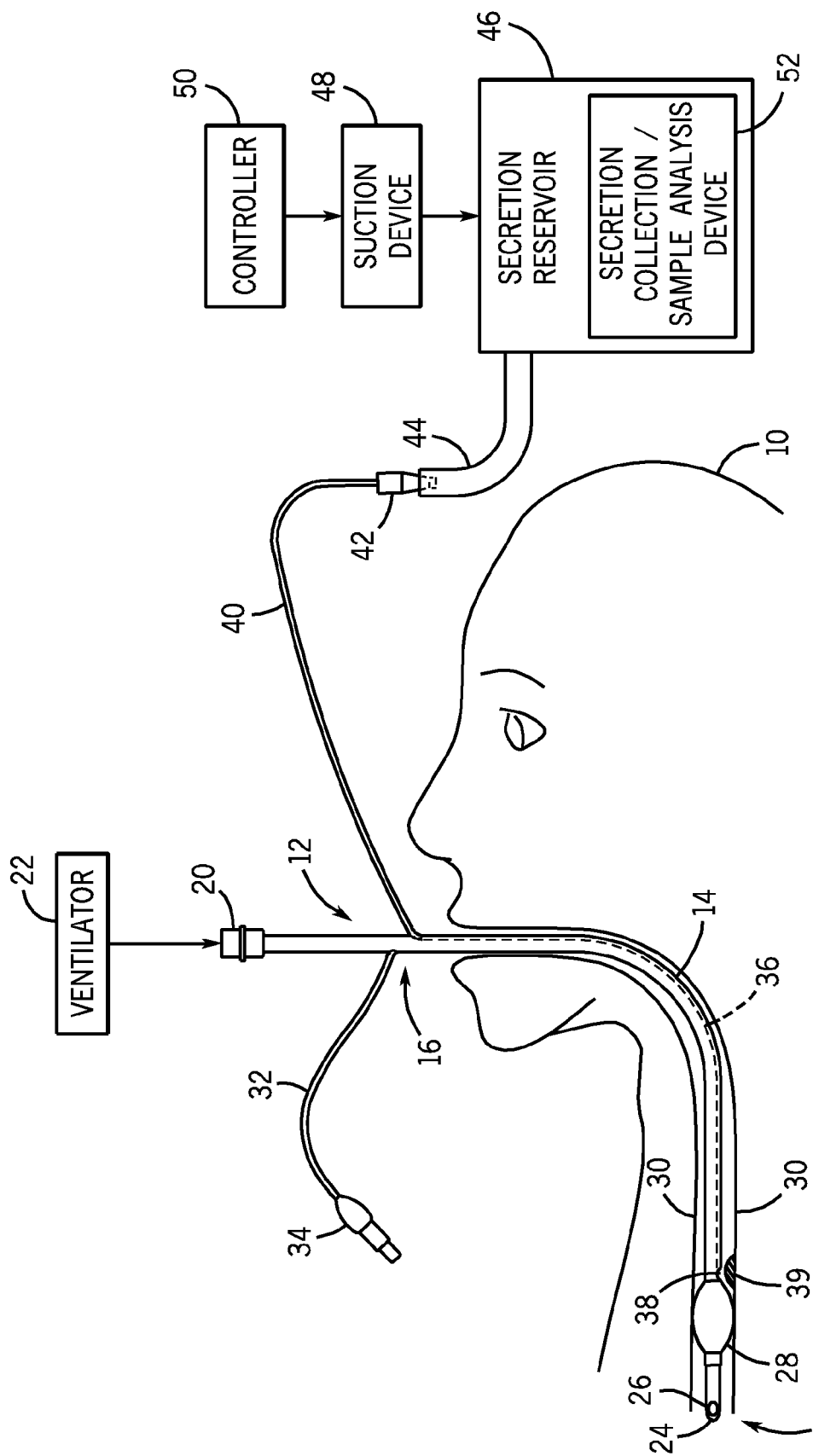
FIG. 3 illustrates an exemplary system including an endotracheal tube connected to a secretion reservoir including a secretion collection and/or sample analysis device in accordance with aspects of the present disclosure.

FIGS. 2 and 3 illustrate further embodiments of the present disclosure in which the location of the device 52 with respect to the endotracheal tube 12 is varied. In the embodiment illustrated in FIG. 2, the device receives samples directly from the evacuation conduit 44 instead of from the secretion reservoir 46 with respect to FIG. 1. In the embodiment illustrated in FIG. 3, the device 52 is located in the secretion reservoir 46 from which it collects samples. Embodiments illustrated in FIGS. 1 and 3 may require mixing of the collected secretions to ensure homogeneity of the solution from which the device 52 collects samples. Additionally, any analysis performed by the devices 52 in the embodiments of FIGS. 1 and 3 that may track the progression of detected pathogen levels over time would require normalization to the first time point, since each secretion sample taken would include the value of prior readings as well as the reading for the time point of interest. The embodiment illustrated in FIG. 2, however, would not require correction for previous time points since the samples are drawn directly into the device 52 from the evacuation conduit 44. During operation, an operator may use a purging system to cleanse the evacuation conduit 44, the suction tube 40, and the suction lumen 36 of possible residual secretion accumulation. For instance, liquid or gas flow through the system may be established to ensure that the flow path from the airway of the patient to the device 52 is clear in between sample collection. Additionally, external components, such as the evacuation conduit 44, may be replaced as desired to minimize the contamination of the collected secretion samples.

Figure 4:
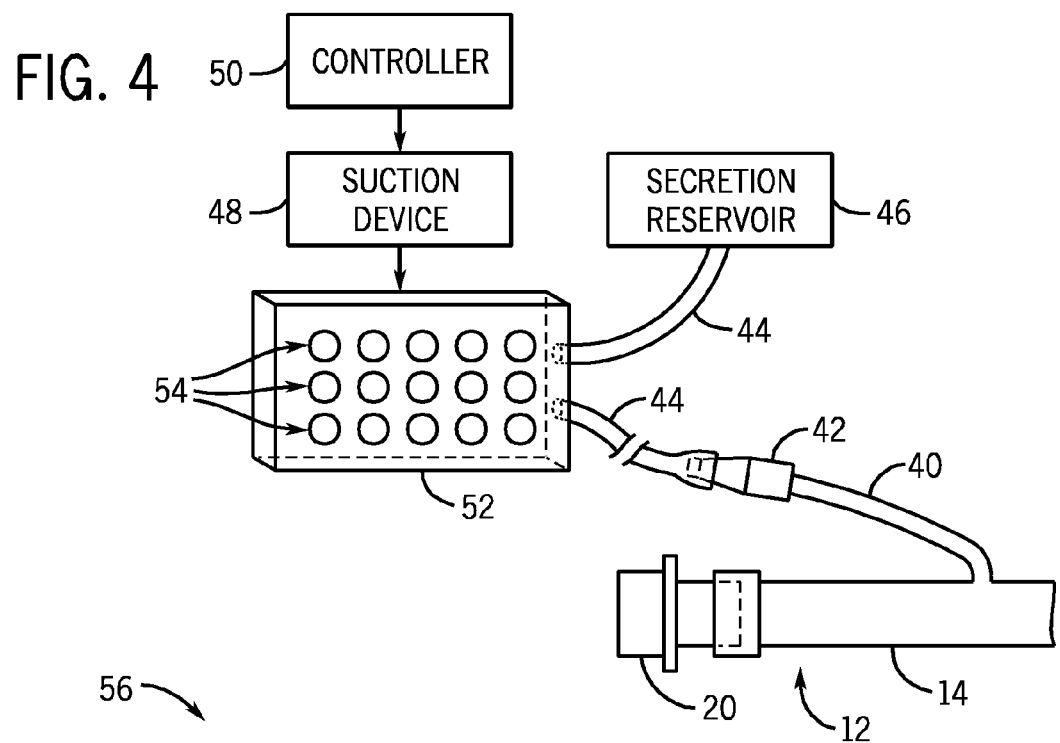
FIG. 4 illustrates an exemplary system including an endotracheal tube connected to a secretion collection device in accordance with aspects of the present disclosure.

FIG. 4 illustrates an exemplary embodiment of the device 52 that may be used for timed secretion collection at the point-of-care. In the illustrated embodiment, the device 52 receives aspirated secretions directly from the evacuation conduit 44. A predetermined volume of each aspirated secretion may be directed to a collection well 54 designated for that time point. The remaining secretion volume at each time point may reenter the evacuation conduit 44 for storage in the secretion reservoir 46. In alternate embodiments, the entire secretion sample collected from the evacuation conduit 44 at each time point may be stored in collection wells 54 and the secretion reservoir 46 may be eliminated. The illustrated embodiment includes three rows of five collection wells 54. However, it should be noted that any number of desired rows and collection wells 54 may be included in alternate embodiments. The device 52 may also include means for regulating temperature in the device 52 to maintain the integrity of the collected secretion samples until analysis can be performed.

Figure 5:
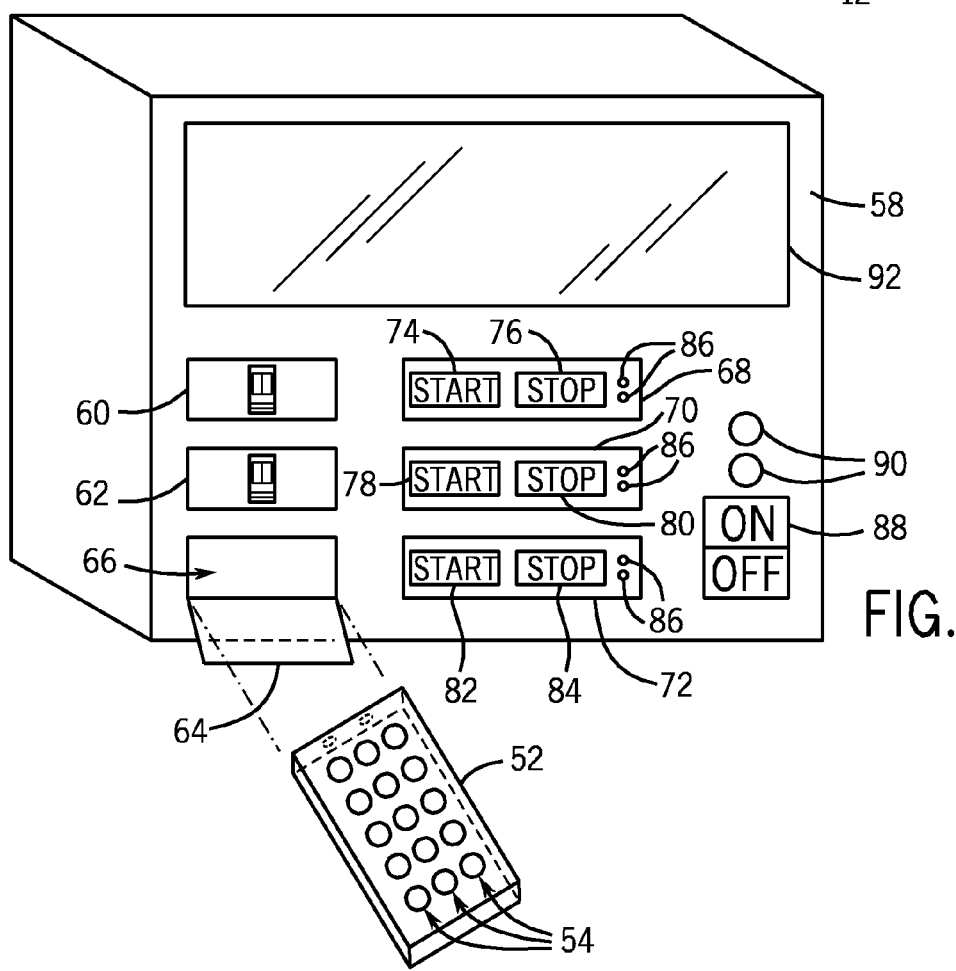
FIG. 5 is a perspective view of an exemplary secretion analysis system in accordance with aspects of the present disclosure.

The exemplary collection device 52 illustrated in FIG. 4 may be used in conjunction with an exemplary analysis device 56, as illustrated in FIG. 5, to collect and analyze secretion samples at the care giving facility. The analysis device 56 may include detection components that are too large to fit on the collection device 52, such as optical cameras or devices. The analysis device 56 may be located at a nurse's station, in a supply room, and so forth. The analysis device 56 may be configured to receive one or more collection devices 52 for processing and analysis. For instance, the analysis device 56 in the illustrated embodiment is configured to receive three collection devices 52. That is, the front panel 58 of the analysis device 56 contains two closed doors 60, 62 and one open door 64 that are configured to cover slots in which collection devices 52 from patients may be placed. For instance, the illustrated collection device 52 may be placed in slot 66 for analysis. It should be noted that although only three slots are illustrated, alternate embodiments may include more or fewer slots as desired. Control panels 68, 70, and 72 correspond to the slots associated with doors 60, 62, and 64, respectively, and allow the operator to control the analysis of the inserted samples. For instance, the control panels 68, 70, and 72 include start and stop buttons 74, 76, 78, 80, 82, and 84 that allow the operator to selectively start and stop the analysis of the samples inserted into each slot. The control panels 68, 70, and 72 may also include buttons or indicator lights 86 that allow the operator to choose from preset analysis programs, inform the operator of the status of a run, and so forth.

The analysis device 56 may also include a power switch 88 configured to allow the operator to power the analysis device 56 on and off as desired. Indicator lights 90 may communicate the status of the analysis device 56, a low power state of the analysis device 56, and so forth. A user interface and display panel 92 may be located on the front panel 58 of the analysis device 56. The user interface and display panel 92 may indicate the overall status of the analysis device 56 (e.g., how much longer each inserted device 52 has left to run) and provide the operator the option of programming a customized analysis program. For instance, if the operator wanted to perform a PCR analysis probing for pathogens associated with uncommon pathologies, the operator may use the user interface and display panel 92 to input parameters such as cycle time, number of cycles, temperature of cycles, and so forth.

Figure 6:
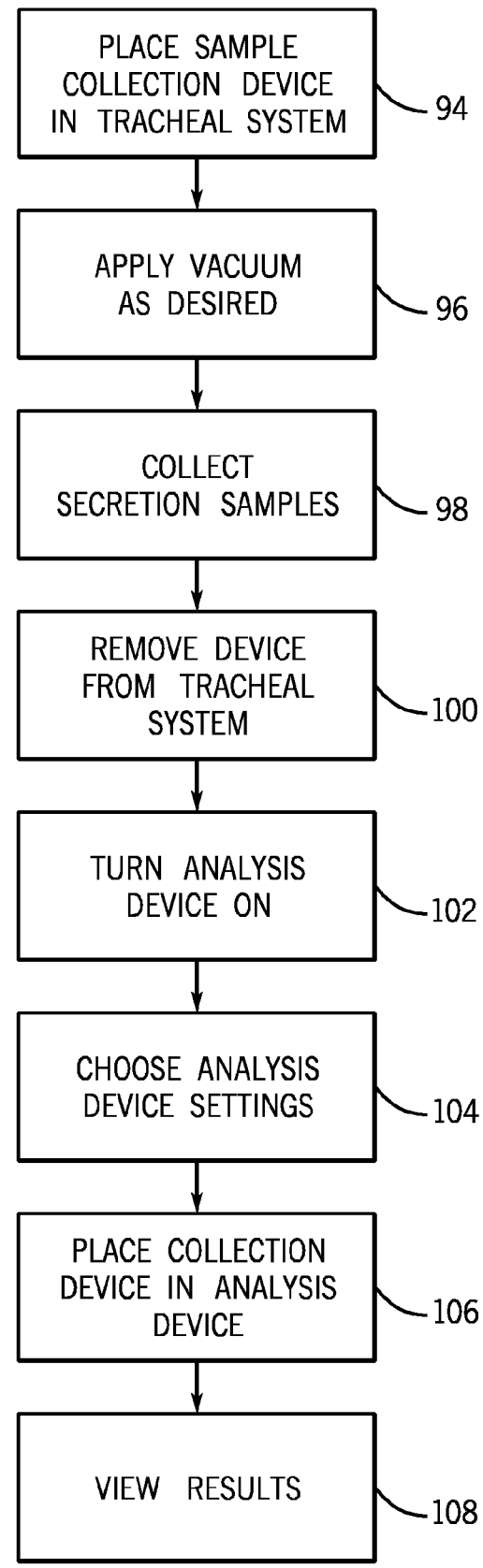
FIG. 6 is a block diagram illustrating exemplary logic that may be used to operate a secretion collection and/or sample analysis device in accordance with aspects of the present disclosure.

FIG. 6 illustrates exemplary logic that may be used to operate the secretion collection device 52 and the analysis device 56 illustrated in FIGS. 4 and 5 in accordance with aspects of the present disclosure. The sample collection device 52 is first placed in the tracheal tube system such that one of the previously illustrated configurations is achieved, as indicated by block 94. The suction device 48 is then activated such that vacuum is applied to the endotracheal tube 12 and secretions may be aspirated from the airway of the patient, as indicated by block 96. Secretion samples may then be collected in the collection device 52 at predetermined time points for the predetermined period of time, as indicated by block 98. When sample collection is complete, the collection device 52 may be removed from the tracheal system, as indicated by block 100. The operator may then power on the analysis device 56, as indicated by block 102, and choose the desired settings, as indicated by block 104. The collection device 52 may then be placed in the analysis device 56 for processing, as indicated by block 106. Finally, the results of the analysis may be viewed by the operator, as indicated by block 108. In this manner, the secretion samples may be collected at the bedside and analyzed in the care giving facility, possibly yielding results in a quicker and more efficient manner than traditional systems.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A tracheal intubation system comprising:
   a tracheal tube comprising a tubular body having an open distal end configured to allow airflow to and from a patient at a point of care, and a suction lumen disposed in a wall of the tubular body;
   an evacuation conduit configured to receive aspirated secretions from the suction lumen at a plurality of time points;
   a plurality of collection wells coupled to the evacuation conduit, wherein a predetermined volume of the aspirated secretions from individual time points is configured to be directed towards respective individual collection wells of the plurality of collection wells;
   a secretion reservoir coupled to the plurality of collection wells, wherein the secretion reservoir is configured to receive a remaining volume of the aspirated secretions from the individual time points, such that only a portion of the aspirated secretions from an individual time point is directed towards a respective individual collection well;
   an analysis device at the point of care that in operation analyzes a plurality of aspirated secretion samples from the respective individual collection wells, each individual sample of the plurality of aspirated secretion samples corresponding to the aspirated secretions received by the evacuation conduit at each of the plurality of time points; and
   a purging system configured to purge the evacuation conduit and the suction lumen of residual secretions between each of the plurality of time points.

2. The tracheal intubation system of claim 1, comprising a suction device configured to apply vacuum to the evacuation conduit such that the aspirated secretions are drawn through the suction lumen and the evacuation conduit.

3. The tracheal intubation system of claim 1, wherein the analysis device is connected in series with the secretion reservoir and the evacuation conduit.

4. The tracheal intubation system of claim 1, wherein the analysis device is a lab-on-a-chip.

5. The tracheal intubation system of claim 1, wherein the analysis device is configured to perform a polymerase chain reaction.

6. The tracheal intubation system of claim 1, wherein the analysis device is configured to indicate the presence or absence of pathogens at a point of care.

7. The tracheal intubation system of claim 1, comprising an analysis system configured to receive the analysis device, perform an analysis, and output results of the analysis at the point-of-care.

8. The tracheal intubation system of claim 1, wherein the purging system is configured to purge the evacuation conduit and the suction lumen by establishing liquid or gas flow through the evacuation conduit and the suction lumen between each of the plurality of time points.

9. The tracheal intubation system of claim 1, wherein the evacuation conduit is coupled to the secretion reservoir and the plurality of collection wells.

\* \* \* \* \*